`US005166074A`

United States Patent [19]
Vessey et al.

[11] Patent Number: 5,166,074
[45] Date of Patent: Nov. 24, 1992

[54] METHOD OF DETECTING THE INITIAL CONCENTRATION OF A WATER-TREATMENT CHEMICAL IN A DILUTED AQUEOUS SYSTEM

[76] Inventors: Adrian M. Vessey, 16 Austin Drive, Didsbury, Manchester M20 0EA; David S. Ryder, 40 Moss Lane, Middleton, Manchester M24 1WT, both of England

[21] Appl. No.: 609,850

[22] Filed: Nov. 7, 1990

[30] Foreign Application Priority Data

Nov. 15, 1989 [GB] United Kingdom ............... 8925876

[51] Int. Cl.$^5$ ............................................ G01N 21/64
[52] U.S. Cl. ....................................... 436/103; 436/56; 436/104; 436/105; 436/172; 422/15; 422/16; 422/17; 422/18; 422/19; 210/709; 210/245; 252/180; 252/408.1
[58] Field of Search ................... 436/18, 56, 165, 171, 436/172, 103–105; 422/3,15–19; 252/180, 408.1; 210/709, 745

[56] References Cited

U.S. PATENT DOCUMENTS 4,342,739  8/1982  Kakimi et al. ...................... 424/1
4,783,314  11/1988  Hoots et al. ......................... 422/3

FOREIGN PATENT DOCUMENTS 0320086  6/1989  European Pat. Off. .

Primary Examiner—James C. Housel
Assistant Examiner—David Redding
Attorney, Agent, or Firm—Luther A. R. Hall

[57] ABSTRACT

A method of detecting the initial concentration of a water-treatment chemical present in a diluted aqueous system, by (1) incorporating into the aqueous system, a mixture including a known amount of the active ingredient and a known amount of an ultra-violet sensitive compound having the formula (I):

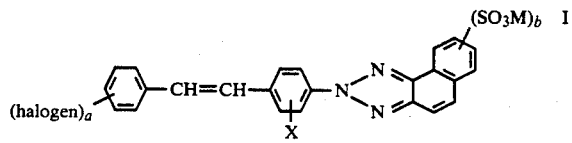

wherein halogen is chlorine or bromine; X is $-CN$, $-SO_3M$, $-SO_2NH-C_2H_5$, $-SO_2NH(CH_2)_3N(CH_3)_2$,

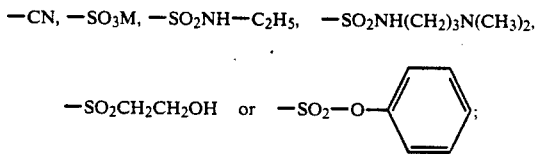

and a and b, independently are 0 or 1; M is hydrogen or an alkaline metal ion; and (2) detecting the concentration of the compound of formula I, by exposing to ultra-violet light a sample of the aqueous system so treated.

9 Claims, No Drawings

METHOD OF DETECTING THE INITIAL CONCENTRATION OF A WATER-TREATMENT CHEMICAL IN A DILUTED AQUEOUS SYSTEM

The present invention relates to a method of detecting the initial concentration of a water treatment chemical in a diluted aqueous system.

In many systems, e.g. aqueous systems, treated with active ingredients, the active ingredient in question may prove difficult to detect in the system. To date, chromates or molybdates have been employed as analyzable tracers in cooling water formulations. The use of these known tracers is indesirable on environmental protection grounds.

More recently, in U.S. Pat. No. 4,783,314, a process of monitoring the acceptable level of a treating component is described, involving adding to the water an inert water-soluble fluorescent tracer, and analyzing a withdrawn sample of the water against a standard.

In order to distinguish the preferred 2-naphthalene sulphonic acid and/or Acid Yellow 7 tracers from background interference, e.g. from aryltriazole corrosion inhibitors for brass, the process of U.S. Pat. No. 4,783,314 requires the use of externally applied excitation energy, and the use of optical apparatus as an aid to detecting the presence of the tracer. 2-Naphthalene sulphonic acid, moreover, does not fluoresce in UV light.

In EP-A-320086, the concentration of a treatment composition in water is detected by adding a known amount of a) a water-soluble dye and b) a known amount of a treatment composition to the water, and then detecting the concentration of composition b) by detecting the concentration of dye a).

The only specific teaching in EP-A-320086 as to suitable water-soluble dyes concerns fluorescein or related compounds.

Fluorescein has the severe disadvantage, which is acknowledged at page 3, lines 26 and 27 of EP-A-320086, that it is degraded in the presence of chlorine which is the cheapest, and therefore most commonly-used biocide, in industrial waters. The chlorine sensitivity is also exhibited by Acid Yellow 7 as mentioned in the above U.S. Pat. No. 4,783,314.

There is therefore a need for an environmentally-safe tracer product, capable of incorporation into cooling water formulations, which is stable especially to chlorine under normal water conditions and which can be analyzed, on site, using simple techniques.

We have now found that certain compounds, previously-known as fluorescent brightening agents for textiles, meet all the requirements for a satisfactory tracer product for active ingredients in various systems, especially aqueous systems.

Accordingly, the present invention provides a method of detecting the initial concentration of an active ingredient present in a diluted aqueous system, comprising (1) incorporating into the aqueous system a mixture comprising a known amount of the active ingredient and a known amount of an ultra-violet sensitive compound having the formula (I):

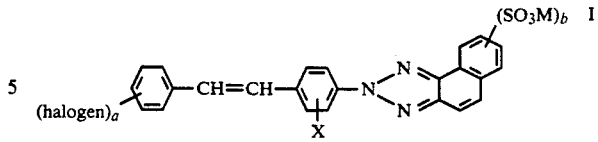

wherein halogen is chlorine or bromine; X is

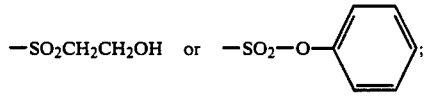

$-SO_2CH_2CH_2OH$ or $-SO_2-O-$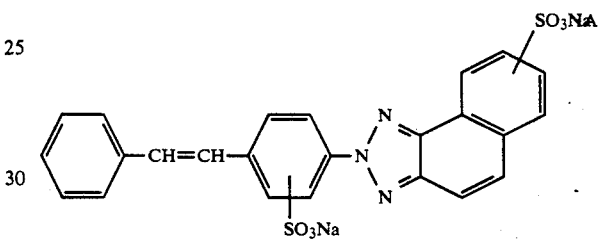;

and a and b, independently, are 0 or 1; M is hydrogen or an alkaline metal ion; and (2) detecting the concentration of the compound of formula I, by exposing to ultra-violet light a sample of the aqueous system so treated.

A particularly preferred compound of formula (I) is that having the formula (IA):

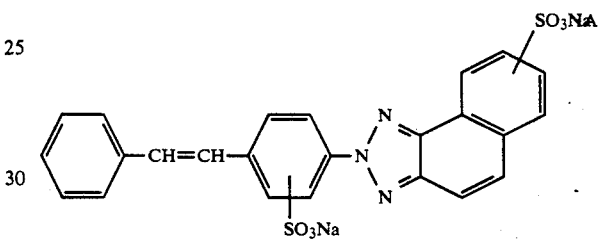

The compounds of formula I are well-known commercially-available fluorescent whitening agents.

The compounds of formula I may be incorporated into the system together with the active ingredient to be detected, or separately prior to adding the active ingredient. Preferably, the compounds of formula I are used in concentrations of from 0.1 to 10 ppm, based on the weight of the water system.

The compounds of formula (I) must, of course, be stable in the presence of contaminants, e.g. chlorine or calcium, present in the system; be stable to chemical attack by the system itself, and to ultra-violet light; be stable in the presence of the active ingredient in question; and must not cause corrosion of the materials used to construct the system.

If the active ingredient is a water treatment chemical in an aqueous system, the compounds of formula (I) have been found to be compatible with (viz. not lost from solution by interaction with) chlorine and bromine and calcium ions present in the water; compatible with organic and inorganic water treatment active ingredients e.g. corrosion inhibitors and scale inhibitor; stable to hydrolysis by the aqueous system; table to ultra violet light; and non-corrosive materials, e.g. to ferrous metals, used to construct containers for aqueous systems.

In addition, the compounds of formula (I) can be readily detected by the eye at concentrations down to 0.25 ppm, when irradiated with ultra-violet light, under working conditions.

The compounds of formula (I) are particularly suitable for use as detectors for organic water-treatment chemicals in aqueous systems, especially aqueous systems containing chlorine.

With respect to aqueous systems which may be treated according to the present invention, of particular interest with respect to combined corrosion inhibition and anti-scale treatments are cooling water systems, steam generating systems, sea-water evaporators, reverse osmosis equipment, paper manufacturing equipment, sugar evaporator equipment, soil irrigation systems, hydrostatic cookers, gas scrubbing systems, closed circuit heating systems, aqueous-based refrigeration systems and down-well systems; for corrosion inhibition treatments alone, aqueous systems of particular interest include aqueous machining fluid formulations (e.g. for use in boring, milling, reaming, broaching, drawings, spinning, turning, cutting, sawing, grinding, and thread-cutting operations or in non-cutting shaping in drawing or rolling operations) aqueous scouring systems, engine coolants including aqueous glycol antifreeze systems, water/glycol hydraulic fluids; and aqueous based polymer surface-coating systems; or solvent-based polymer systems, e.g. those containing tetrahydrofuran, ketones or alkoxyalkanols.

In the treatment of systems which are completely aqueous, such as cooling water systems, air-conditioning systems, steam-generating systems, sea-water evaporator systems, hydrostatic cookers, and closed circuit heating or refrigerant systems, the water treatment chemicals to be detected may be e.g. corrosion inhibitors such as, for example, water soluble zinc salts; phosphates; polyphosphates; phosphonic acids and their salts, for example, hydroxyethyl diphosphonic acid (HEDP), nitrilotris-methylene phosphonic acid and methylamino dimethylene phosphonocarboxylic acids and their salts, for example, those described in DE-A-2632774, hydroxy-phosphonoacetic acid, 2-phosphonobutane-1,2,4-tri-carboxylic acid and those disclosed in GB-A-1572406; nitrates, for example, sodium nitrate; nitrites, e.g. sodium nitrite; molybdates, e.g. sodium molybdate; tungstates; silicantes, e.g. sodium silicate; benzotriazole, bis-benzotrizole or copper deactivating benzotriazole or tolutriazole derivatives or their Mannich base derivatives; mercaptobenzotriazole; N-acyl sarcosines; N-acylimino diacetic acids; ethanolamine; fatty amines; and polycarboxylic acids, for example, polymaleic acid and polyacrylic acid, as well as their respective alkali metal salts, copolymers of maleic anhydride, e.g. copolymers of maleic anhydride and sulfonated styrene, copolymers of acrylic acid, e.g. copolymers of acrylic acid and hydroxyalkylated acrylic acid, and substituted derivatives of polymaleic and polyacrylic acids and their copolymers. Moreover, in such completely aqueous systems, the water treatment chemical for detection according to the invention may comprise dispersing and/or threshold agents, e.g. polymerised acrylic acid (or its salts), phosphinopolycarboxylic acids (as described and claimed in GB-A-1458235), the cotelomeric compounds described in EP-A-0150706, hydrolysed polyacrylonitrile, polymerised methacrylic acid and its salts, polyacrylamide and copolymers thereof from acrylic and methacrylic acids, lignin sulphonic acid and its salts, tannin, naphthalene sulphonic acid/ formaldehyde condensation products, starch and its derivatives, cellulose, acrylic acid/lower alkylhydroxy-acrylate copolymers, e.g. those described in U.S. Pat. No. 4,029,577, styrene/maleic anhydride copolymers and sulfonated styrene homopolymers, e.g. those described in U.S. Pat. No. 4,374,733 and combinations thereof. Specific threshold agents, such as for example, 2-phosphono-butane-1,2,4-tri-carboxylic acid (PBSAM), hydroxyethyl diphosphonic acid (HEDP), hydrolysed polymaleic anhydrie and its salts, alkyl phosphonic acids, hydroxyphosphonoacetic acid, 1-aminoalkyl-1,1-diphosphonic acids and their salts, and alkali metal polyphosphates, may also be used.

Particularly interesting water treatment chemical additive packages are those comprising one or more of polymaleic acid or polyacrylic acid or their copolymers, or substituted copolymers, hydroxyphosphonoacetic acid, HEDP, PBSAM, triazoles such as tolutriazole, molybdates and nitrites.

The water treatment chemical may also comprise one or more of precipitating agents such as alkali metal orthophos-phates, carbonates; oxygen scavengers such as alkali metal sulphites and hydrazines; sequestering agents such as nitrilotriacetic acid and its salts; anti-foaming agents such as silicones, e.g. polydi-methylsiloxanes, distearylsebacaide, distearyl adipamide and related products derived from ethylene oxide and/or propylene oxide condensations, in addition to fatty alcohols, such as capryl alcohols and their ethylene oxide condensates; and biocides, e.g. amines, quaternary ammonium compounds, chloro-phenols, sulphur-containing compounds such as sulphones, methylene bis thiocyanates and carbamates, isothiazolones, brominated propionamides, triazines, phosphonium compounds, chlorine and chlorine-release agents and organometallic compounds such as tributyl tin oxide.

The following Examples further illustrate the present invention.

EXAMPLE 1

Preparation of an alkaline corrosion inhibiting formulation containing a sulphonated stilbenyl naphthazole as marker

| Formulation | |
| --- | --- |
| 2-hydroxyphosphonoacetic acid | 5.0 g as solids |
| Maleic anhydride/vinyl acetate/ethyl acrylate terpolymer | 2.5 g as solids |
| Tolutriazole (TTA) | 2.0 g |
| sulphonated stilbenyl naphthazole of formula (IA) | 0.5 g as product |
| 30% sodium hydroxide solution to bring the formulation to pH 10.0<br>Water | to 100 g |

Preparation Procedure

Depending on their solids contents, appropriate weights are taken to give 5.0 g 2-hydroxy-phosphonoacetic acid and 2.5 g maleic anhydride/vinyl acetate-/ethyl acrylate terpolymer solids.

These are mixed together with about 40 g water and sufficient 30% sodium hydroxide is added to bring the pH to 10.0.

2.0 g TTA is then dissolved in about 25 g water by warming, and this solution added to the first mix, the pH-value once again being adjusted to 10.0 with 30% sodium hydroxide.

Finally, 0.5 g of the sulphonated stilbenzyl naphthazole of formula (IA) is added and dissolved in the slightly warmed mixture, which is made up to 100 g with water.

Dilution of the above formulation and measurement of the sulphonated stilbenyl naphthazole level by ultra-violet light (UV)

1 g of the above formulation is diluted in distilled water to 100 ml.

1 ml portions of this diluted formulation are further diluted to 100 ml in
a) Distilled water
b) Standard hardwater (Newton, Manchester, U.K.);
c) Typical plant cooling water The concentration of sulphonated stilbenyl naphthazole in these final dilutions of the formulation should be 0.5 ppm.

This is checked in a UV viewer against standard solutions prepared in distilled water of 0.4 ppm an d0.6 ppm sulphonated stilbenzyl naphthazole respectively. In each case it is possible to see the naked eye that the fluorescence of each of the these formulation dilutions lay between that of the two standards.

EXAMPLE 2

Evaluation of chlorine sensitivity

A) Calibration of the fluorimeter

A fluorimeter (FM 3 Mark I) is calibrated against a range of concentrations of the compound of formula (IA) in distilled water.

The instrument is calibrated so that a concentration of 10 ppm of the compound of formula (IA) gives an instrument reading of 100, and distilled water containing no additive gives an instrument reading of zero.

The instrument is then used to determine the fluorimeter readings for concentrations of 5.0, 2.5 and 1.0 ppm of the compound of formula (IA). The results are set out below:

| ppm | Fluorimeter reading (no filter) | After 1 day |
| --- | --- | --- |
| 10.0 | 100 | 100 |
| 5.0 | 86 | 86 |
| 2.5 | 70 | 70 |
| 1.0 | 50 | 50 |

B) Chlorine sensitivity evaluation

Using the procedure described under A), a fluorimeter reading is obtained for a concentrations of 2 ppm of compound of formula (IA). To this solution is then added sufficient sodium hypochlorite to provide 2 ppm of chlorine in the test solution. The solution is then evaluated in the fluorimeter.

The results are as follows:

| ppm | Fluorimeter reading | After 1 day |
| --- | --- | --- |
| 10.0 | 100 | 100 |
| 2.0 | 64 | 64 |
| 2.0 / 2.0 chlorine | 64 | 61 |

EXAMPLE 3

A standard stock solution is made up in distilled water containing 0.05% NaHCO$_3$ and 1 g/100 ml of Ca$^{++}$ions (as CaCO$_3$).

After calibrating the instrument in the manner described in Example 2, fluorimeteric readings are obtained in relation to various solutions containing the compound of formula (IA) and, optionally, Ca$^{++}$ions, as indicated in the following Table:

| Compound of formula (IA) ppm | Ca$^{++}$ (as CaCO$_3$) ppm | Fluorimeter reading (no filter) |
| --- | --- | --- |
| 10.0 | 0 | 100 |
| 2.0 | 0 | 65 |
| 2.0 | 50 | 65 |
| 2.0 | 100 | 65 |
| 2.0 | 200 | 65 |
| 2.0 | 300 | 65 |
| 2.0 | 500 | 65 |
| 2.0 | 1000 | 65 |

The presence of CaCO$_3$ in amounts up to 1000 ppm has no significant effect on the fluorescence of the compound of formula (IA).

We claim:

1. A method of detecting the initial concentrations of a water-treatment chemical present in a diluted aqueous system which comprises
   incorporating into the aqueous system a mixture comprising a known amount of the water-treatment chemical and a known amount of an ultra-violet sensitive compound of formula (I)

wherein halogen is chlorine or bromine; X is $-CN$, $-SO_3M$, $-SO_2NH-C_2H_5$, $-SO_2NH(CH_2)_3N(CH_3)_2$, $-SO_2CH_2CH_2OH$ or $-SO_2-O-\phenyl$;

a and b are independently 0 or 1; and M is hydrogen or an alkaline metal ion; and
detecting the concentration of the compound of formula (I) by exposing to ultra-violet light a sample of the aqueous system so treated and measuring the fluorescence of said sample, and therefor concomitantly determining the initial concentration of the water-treatment chemical in the diluted aqueous system.

2. A method according to claim 1, wherein the compound of formula (I) is a compound of formula (IA):

3. A method according to claim 1 wherein the water-treatment chemical added to the aqueous system is an organic chemical.

4. A method according to claim 1 wherein the aqueous system contains chlorine.

5. A method according to claim 3 wherein the aqueous system is a cooling water system, a steam generating system, a sea-water evaporator, reverse osmosis equipment, paper manufacturing equipment, sugar evaporator equipment, a soil irrigation system, a hydrostatic cooker, a gas scrubbing system, a closed circuit heating system, an aqueous-based refrigeration system or a down-well system.

6. A method according to claim 3 wherein the water treatment chemical to be detected is a corrosion inhibitor.

7. A method according to claim 3 wherein the water treatment chemical for detection comprises one or more of dispersing and threshold agents.

8. A method according to claim 3 wherein the water treatment chemical is one or more of polymaleic acid or polyacrylic acid or their copolymers, or substituted copolymers, hydroxyphosphonoacetic acid, HEDP, PBSAM, triazoles, moylbdates and nitrates.

9. A method according to claim 3 wherein the water treatment chemical also comprises one or more of precipitating agents, oxygen scavengers, sequestering agents, anti-foaming agents and biocides.

* * * * *

UNITED STATES PATENT AND TRADEMARK OFFICE
CERTIFICATE OF CORRECTION

PATENT NO. : 5,166,074

DATED : Novenber 24, 1992

INVENTOR(S) : Adrian Michael Vessey and David Stephen Ryder

It is certified that error appears in the above-identified patent and that said Letters Patent is hereby corrected as shown below:

Column 2, between lines 23 and 25, "$SO_3NA$" should read --$SO_3Na$--. Column 6, between lines 53 and 55, "$SO_3NA$" should read --$SO_3Na$--.

Signed and Sealed this

Twenty-third Day of November, 1993

Attest:

BRUCE LEHMAN

Attesting Officer

Commissioner of Patents and Trademarks